United States Patent [19]

Anninos et al.

[11] Patent Number: 5,496,258

[45] Date of Patent: * Mar. 5, 1996

[54] ELECTRONIC DEVICE FOR TREATING EPILEPTIC INDUVIDUALS

[76] Inventors: Photios Anninos, 20 Ellispontou Str., Alexandroupolis; Nicolaos Tsagas, L. THrakos 3, Xanthi; Panayiotis Koutsikos, Demertzi IO, Athens, all of Greece

[ * ] Notice: The portion of the term of this patent subsequent to Jun. 24, 2013, has been disclaimed.

[21] Appl. No.: 90,020

[22] PCT Filed: Jul. 25, 1991

[86] PCT No.: PCT/GR91/00011

§ 371 Date: Jun. 24, 1993

§ 102(e) Date: Jun. 24, 1993

[30] Foreign Application Priority Data

Aug. 24, 1990 [GR] Greece ................. 900100630

[51] Int. Cl.⁶ .................................................. A61N 1/00
[52] U.S. Cl. ........................................................ 600/13
[58] Field of Search ............................................ 600/9–15

[56] References Cited

U.S. PATENT DOCUMENTS 4,066,065  1/1978  Kraus ........................... 600/13
4,940,453  7/1990  Cadwell .

FOREIGN PATENT DOCUMENTS 0084019  7/1983  European Pat. Off. .
0099734  2/1984  European Pat. Off. ............ 600/14
2707574  8/1978  Germany .
333197   3/1985  Germany ........................... 600/14
2156679  10/1985 United Kingdom ................ 600/14

OTHER PUBLICATIONS

"The Art of Measurement: Metrology in fundamental and applied physics" Bernhard Kramer (editor); 1988, VCH, Weinheim (DE) New York (US); M. Hoke, SQUID–based measuring techniques—A challenge for the functional diagnostics in medicine see pp. 287–333.

Primary Examiner—Angela D. Sykes
Assistant Examiner—John P. Lacyk
Attorney, Agent, or Firm—Dowell & Dowell

[57] ABSTRACT

A device suitable for treating epileptic individuals to inhibit epileptic seizures is disclosed. The device utilizes information pertaining to the location and characteristics of an epileptic individual's epileptic foci as determined by a SQUID, and applies magnetic fields to the foci of an appropriate intensity and frequency to inhibit seizure activity.

15 Claims, 5 Drawing Sheets

Left

| 38 | 37 | 36 | 35 | 34 | 33 | 32 | 31 |
|----|----|----|----|----|----|----|----|
| ◎  | ◎  | ◎  | ◎  | ◎  | ◎  | ◎  | ◎  |
| 28 | 27 | 26 | 25 | 24 | 23 | 22 | 21 |
| ◎  | ◎  | ◎  | ◎  | ◎ $T_3$ | ◎ | ◎ | ◎ |
| 18 | 17 | 16 | 15 | 14 | 13 | 12 | 11 |
| ◎  | ◎  | ◎  | ◎  | ◎  | ◎  | ◎  | ◎  |
| 08 | 07 | 06 | 05 | 04 | 03 | 02 | 01 |
| ◎  | ◎  | ◎  | ◎  | ◎  | ◎  | ◎  | ◎  |

Right

| 31 | 32 | 33 | 34 | 35 | 36 | 37 | 38 |
|----|----|----|----|----|----|----|----|
| ◎  | ◎  | ◎  | ◎  | ◎  | ◎  | ◎  | ◎  |
| 21 | 22 | 23 | 24 | 25 | 26 | 27 | 28 |
| ◎  | ◎  | ◎  | ◎ $T_4$ | ◎ | ◎ | ◎ | ◎ |
| 11 | 12 | 13 | 14 | 15 | 16 | 17 | 18 |
| ◎  | ◎  | ◎  | ◎  | ◎  | ◎  | ◎  | ◎  |
| 01 | 02 | 03 | 04 | 05 | 06 | 07 | 08 |
| ◎  | ◎  | ◎  | ◎  | ◎  | ◎  | ◎  | ◎  |

FIG. 1

ELECTRONIC DEVICE FOR TREATING EPILEPTIC INDUVIDUALS

BACKGROUND OF THE INVENTION

The present invention is an electronic device for smoothing dysfunctions of the central nervous system in combination with the use of a Biomagnetometer SQUID. The electronic device comprises a generator of alternating voltage and low frequency which can produce a given frequency from 2 to 7 Hz and which supplies a given number of selected coils from one or more groups of similar coils for the production of alternating magnetic fields. The intensity of the magnetic fields is regulated by microprocessors. A plurality of generators of alternating voltage and low frequency may be provided. Each of the generators can produce a frequency from 2 to 7 Hz and can supply simultaneously a definite number of selected coils for the production of alternating magnetic fields, having a regulated intensity and frequency by microprocessors. The magnetic fields which are simultaneously produced from the coils must be parallel to the alternating magnetic fields which are emitted from the epileptic foci of the brain. The power spectra and frequencies of the emitted magnetic fields of the coils are of the order of the magnetic fields which are emitted from the epileptic foci, that is from 0.5 pT to 7.5 pT. The limit of the intensities can be extended. Satisfactory results can be obtained using 64 similar coils, which is the number of the measuring points of the left and right brain hemispheres. The epileptic foci are first localized with the use of the SQUID. The present electronic device is adjusted with the use of the SQUID, which gives all of the characteristics of the epileptic foci or any other brain malfunction. Thus, the first step is to localize the epileptic foci with the use of the SQUID, and then to adjust properly the electronic device of the present invention according to the characteristic properties of the localized epileptic foci.

SUMMARY OF THE INVENTION

Prior to the present invention were the following publications by the present inventors P. A. Anninos and N. F. Tsagas: *Brain Research Bulletin,* Vol. 16, 1986, and *International Journal of Neuroscience,* Vol. 37, 1987. The device according to the present invention solves the problem of smoothing the epileptic foci or any other dysfunctions of the central nervous system without the use of the known invasive methods. It is perfectly safe because the applied alternating magnetic fields are of low frequency (from 2–7 Hz) and low intensity (from 0.5 pT to 7.5 pT). This problem is solved with the use of either of one generator of low alternating voltage and frequency which can produce a given frequency from 2–7 Hz, and which supplies a given number of selected coils, to produce alternating magnetic fields of which the intensity and frequency are regulated by microprocessors, or with the use of multiple generators of low alternating voltage and frequency which can each produce a frequency from 2–7 Hz and can supply simultaneously a given number of selected coils for the production of alternating magnetic fields of which the intensity and frequency are adjusted using microprocessors.

The device is activated with the necessary characteristic elements of the epileptic foci, which are obtained with the use of the biomagnetometer SQUID, and which are properly stored in an integrated circuit of a microprocessor. The proper storage of the data is done using proper software which is written in basic computer language by the present inventors. The computer program reads the data which are stored on the computer disk or diskette during the analysis of the data recorded from the epileptic foci of a patient with the use of the SQUID for all of the 64 or 128 points of skull. These data are stored with the software program in one matrix with three columns, where in the first column are stored the left temporal or occipital or frontal points, and in the other two columns are stored the frequencies and intensities of the magnetic fields which are emitted from each point. The same is done for the right temporal, occipital and frontal regions of the skull. The correspondence between the points is shown in TABLE A and FIG. 1. With the above-described microprocessor placed in the electronic device, its activation results in that every coil emits an alternating square wave magnetic field of a given frequency and intensity as is shown in FIG. 2. The figures were obtained by checking every coil using the SQUID, so as to obtain first the wave form of the emitted magnetic field (FIG. 2A) and the corresponding power spectrum (FIG. 2B), which gives the fundamental frequency which is emitted from the coil and which must be the same as the frequency and power of the magnetic field which is emitted from the epileptic focus of the corresponding measured point as is stored in the diskette.

The advantage of this method over using a keyboard which would be required in order to enter the data of the epileptic foci and to store them is that the human factor is avoided which otherwise could result in faulty storage of the characteristics of epileptic foci, and furthermore the storage is performed faster depending on the computer running time of the software.

BRIEF DESCRIPTION OF THE DRAWINGS

In the accompanying drawings:

FIG. 1 illustrates the arrangement of measuring points of the left and right temporal hemisphere, respectively, and the reference points T3 and T4, respectively.

DETAILED DESCRIPTION OF THE PREFERRED EMBODIMENT

Figures 2A, 2B:
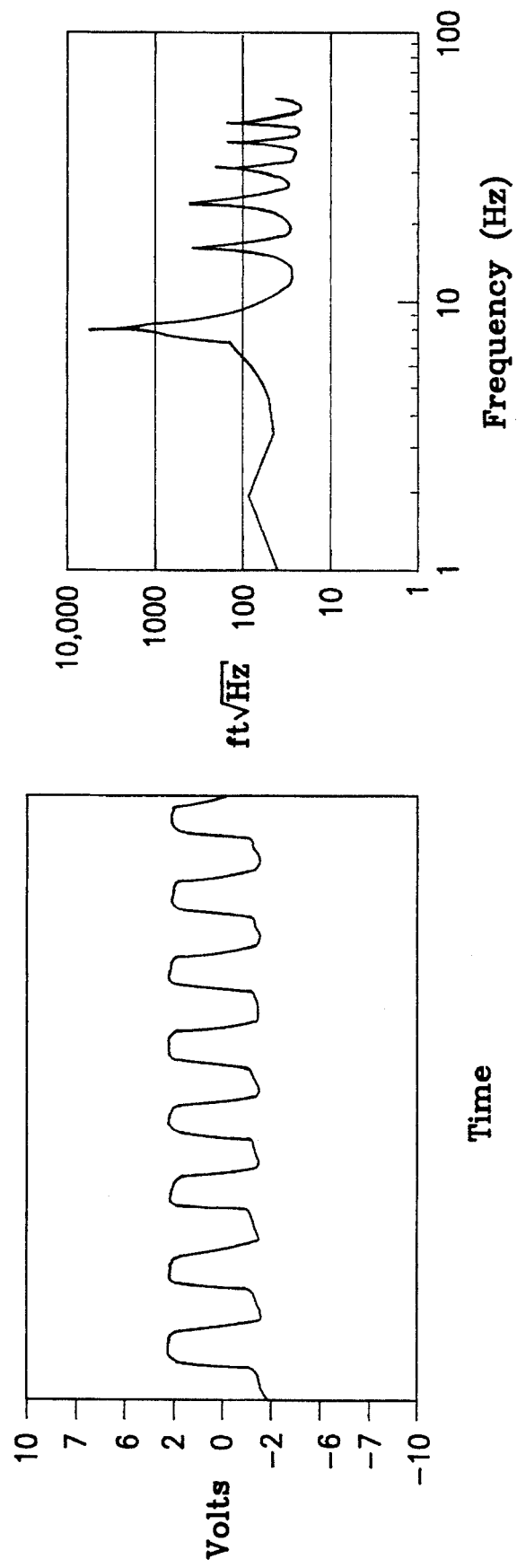
FIG. 2A shows the waveform of the magnetic field which is emitted from one of the coils of the electronic device of the present invention as was recorded by the biomagnetometer SQUID.
FIG. 2B shows the power spectrum of the wave form of FIG. 2A.

The present invention is an electronic device, for the smoothing of dysfunctions of the central nervous system in conjunction with a biomagnetometer SQUID. The device comprises one generator of regulated alternating low voltage which produces a given frequency from 2–7 Hz, and which supplies a number of selected coils of one or more groups of similar coils properly arranged to produce alternating magnetic fields. The magnetic fields may be of different wave forms, and the intensity and frequency of the magnetic fields are regulated by microprocessors or multiple generators of regulated alternating low voltage. Each of the multiple generators produces a frequency from 2–7 Hz and the generators supply simultaneously a number of selected coils of one or more groups of similar coils properly arranged in series, which produce alternating magnetic fields of different possible wave forms. The intensity and frequency of the magnetic fields are regulated by microprocessors. The magnetic fields have similar characteristics to those magnetic fields emitted by the epileptic foci, which are determined using the biomagnetometer SQUID.

The effectiveness of the present invention is based on the necessity to use the biomagnetometer SQUID, at least in the first smoothing of the patient during which the first calibration of the electronic device is performed. Points which form one point matrix of rectangular shape (FIG. 1) are placed around the reference points of the 10–20 International Point System for Electrode Placement. The reference points are T3, T4, P3, P4, F3 and F4 for the left or right temporal hemisphere, the left or right occipital regions, and the left or right frontal brain regions, respectively. Thirty-two points are placed on a plastic hat which is placed on the skull of the patient whose reference points have been defined. The thirty-two points are equally spaced by 1.5 cm from each other and are placed at perfectly defined positions on the skull based on the previously defined coordinates of the reference points. By knowing the coordinates of the reference points, then the coordinates of all thirty-two points of the map and, therefore, the coordinates of the epileptic foci are known.

The SQUID sensor is placed 3 mm above each measuring point and thirty-two consecutive records of one second duration are taken from each point and are digitized with a sampling frequency of 256 Hz. Then, Fourier statistical analysis is performed to find the power spectrum of the magnetic amplitude distribution for a given frequency, or a given range of frequencies, using electronic computer techniques. All equal-power spectra amplitudes for a given frequency, or a given frequency domain, are connected to construct ISO-SA maps. From these maps, and from the density of the ISO contour lines, conclusions can be made as to whether epileptic foci are present, as well as their coordinates and spectra power amplitudes. Finally, from this analysis, once the epileptic foci have been localized with the help of spectral analysis, the frequency of the magnetic field emitted from each epileptic foci can be found. These data are stored on a computer diskette, from which with proper software are stored in one microprocessor. Using the microprocessor, it is possible to energize the present electronic device in order to emit back alternating magnetic fields of similar characteristics as those which are emitted from the epileptic foci. Thus, the present device is completely related with the measurements of the SQUID, which is necessary for the calibration of the device. The present electronic device accomplishes in a direct and non-invasive manner the smoothing of the epileptic foci.

The smoothing of epileptic foci using a microprocessor and software eliminates the human factor for the data transfer from the diskette to the microprocessor and, therefore, avoids errors and saves time because the data transfer is accomplished with the computer system. The smoothing and cancellation of epileptic foci remains for several days or months and is based on the influence of the external varying magnetic field, which induces an inhibitory potential in the neuron synapses in the brain regions where the present electronic device is applied.

Figure 4:
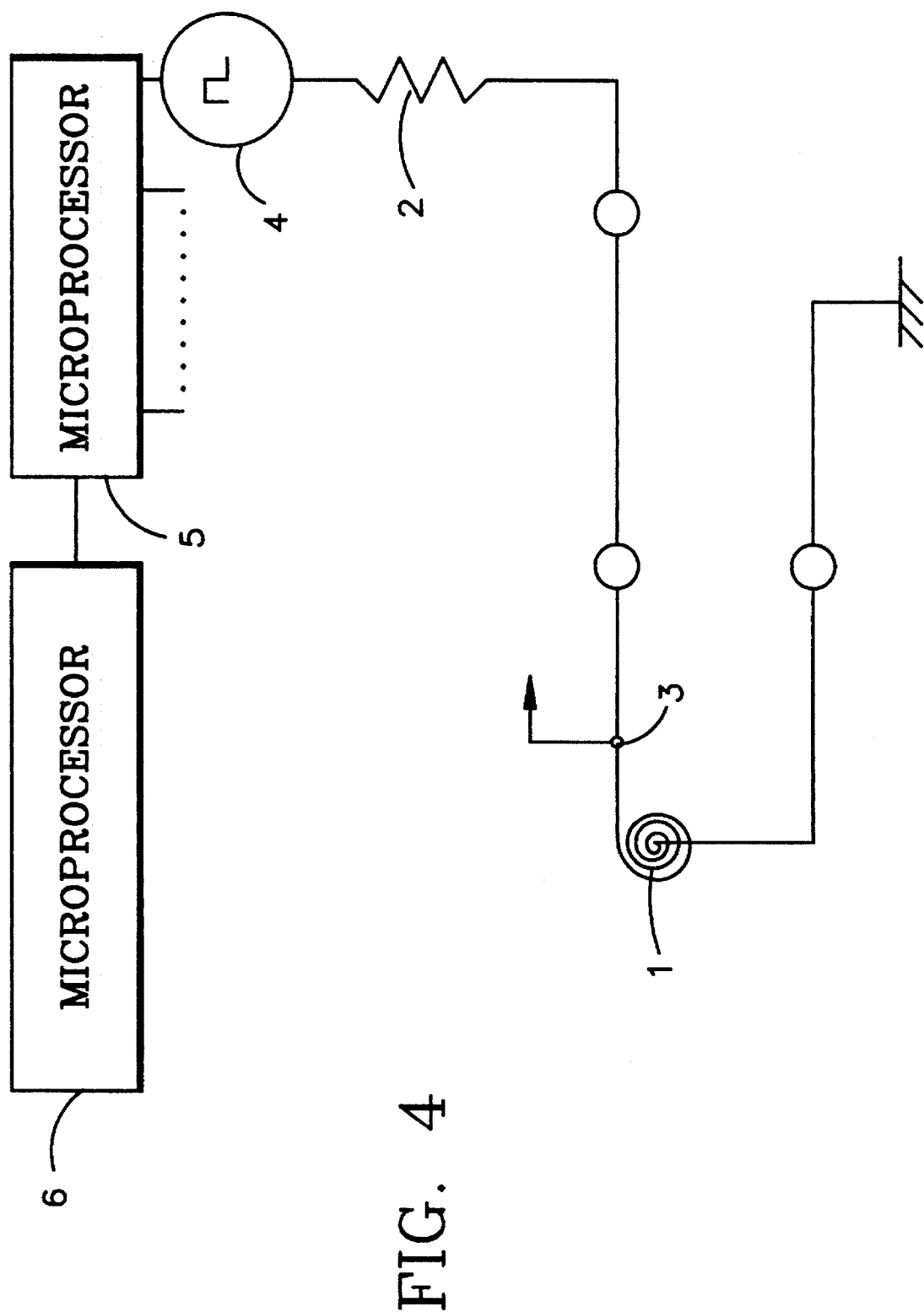
FIG. 4 is a schematic diagram of a circuit of the electronic device in accordance with the present invention.

The electronic device comprises m×n circuits, where m is the number of spiral coils made of a flexible metal or alloy of a proper specific resistance which are mounted on n plates made of appropriate flexible material of high strength. The number m can be less than, equal to or more than thirty-two, and the number n can be less than, equal to, or more than four. Referring to FIG. 4, each of the circuits is comprised of a spiral coil 1 of which one end is grounded and the other end is connected to an alternating current generator 4 through a resistor 2 and a contact-breaker sensor 3 which activates an alarm system. All the circuits are controlled by a microprocessor 5 which selects and energizes all of the nearest coils to the epileptic foci. These coils are supplied with an alternating current which has all of the appropriate characteristics; namely square or some other wave form, and an amplitude and frequency which have been found to be emitted from the epileptic foci using the biomagnetometer SQUID. All these characteristics are controlled by the microprocessor 5.

The device of the present invention comprises a second integrated circuit of a microprocessor 6 which controls the first microprocessor 5 to apply an alternating current of appropriate waveform, amplitude and frequency to the appropriate selected coils which are nearest to the epileptic foci, and, therefore, to generate the appropriate alternating magnetic fields. Also, the second microprocessor 6 controls any faults of the device and the appropriate selection of the coils which must be supplied by the appropriate alternating current.

Figure 5:
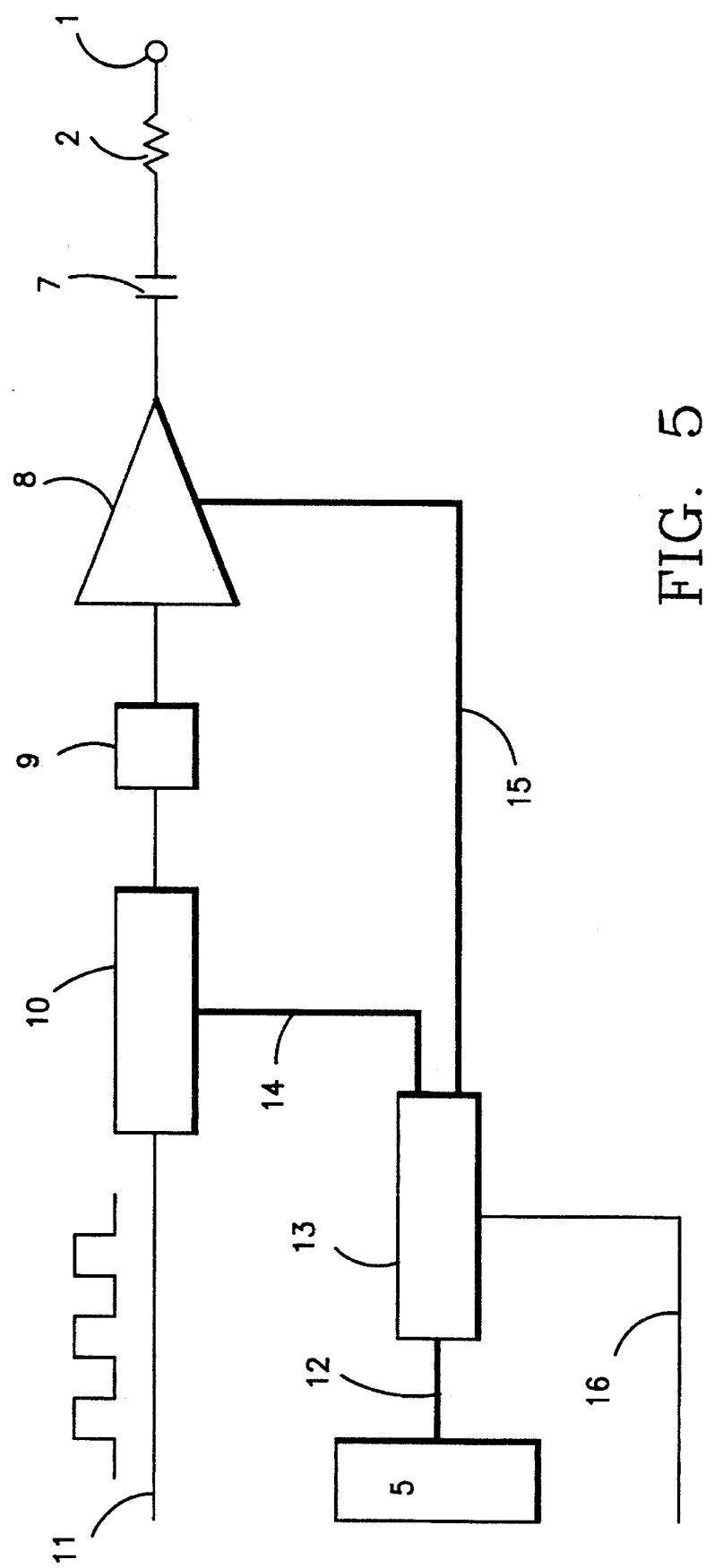
FIG. 5 is a block diagram of one of the identical stages used in the present invention.

Referring to FIG. 5, the individual frequency and amplitude may be set for each pulse train of each spiral coil 1 using a programmable frequency divider 10 and a programmable gain analogue amplifier 8.

FIG. 1 illustrates the arrangement of the thirty-two measuring points of the left and right temporal hemisphere, as well as their respective reference points T3 and T4. The same arrangement of the points is used for the measurements of the frontal and occipital hemispheres of an individual.

FIG. 2A shows the waveform of the magnetic field which was emitted from one of the sixty-four coils of an electronic device in accordance with the present invention, for the time interval of one second, as was recorded by the SQUID. As shown, the frequency of the emitted magnetic field is 8 Hz.

FIG. 2B shows the power spectrum of the wave form of FIG. 2A, from which is seen the power amplitude and frequency which was emitted from one of the sixty-four coils, as recorded by the SQUID.

Figure 3:
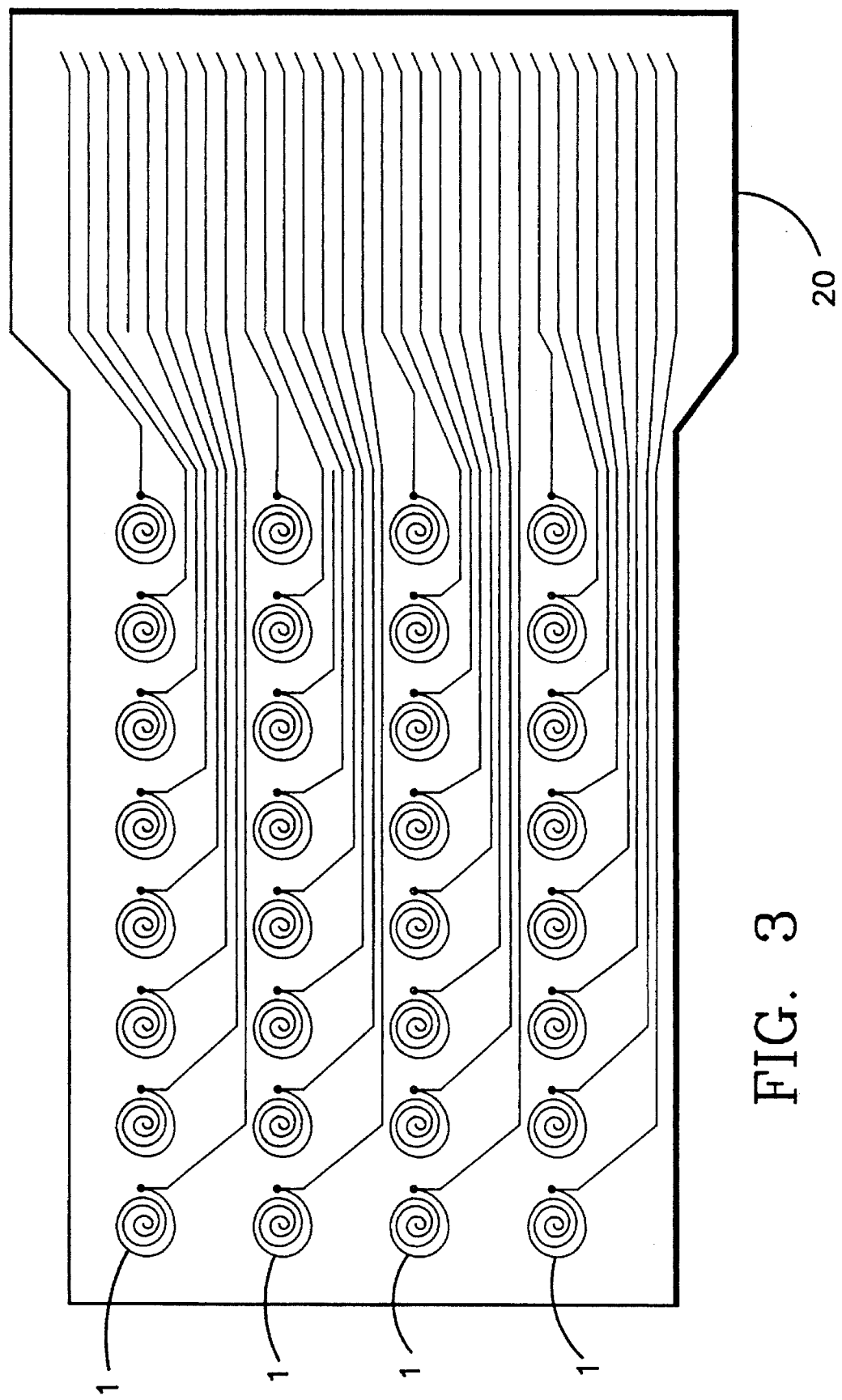
FIG. 3 shows the spiral form and the arrangement of the coils which are used for each hemisphere for smoothing of epileptic foci.

FIG. 3 shows the spiral form and the arrangement of the thirty-two coils 1 which are used for each hemisphere for smoothing of epileptic foci. The coils are located on a flexible plate 20.

FIG. 4 shows the assembly circuit of the spiral coil 1, which is one of the coils on the flexible plate shown in FIG. 3. The resistor 2 of the circuit can have the approximate value of 100 kΩ. The circuit includes a contact-breaker sensor 3 which activates an alarm-system. As explained above, the number of circuits is defined by the number of the coils. The circuit is supplied with an alternating current of square wave or some other wave form 4 which is controlled by the microprocessor 5. This microprocessor controls all of the coils. Also, the microprocessor 5 selects and energizes all the nearest coils to the epileptic foci. These coils are supplied by an alternating current, whose amplitude and frequency are also controlled by the microprocessor 5. The second microprocessor 6 controls the first microprocessor 5 and, in general, controls the normal operation of the device.

FIG. 5 is a block diagram of one of the sixty-four identical stages used in the electronic system. Each one of these stages generates a pulse train of specific frequency and amplitude which drives one of the coils. All the stages are connected to a clock input 11 and to a data bus 12 of the microprocessor 5. Each one of the sixty-four stages is also connected to a dedicated enable line 16. As soon as one enable line 16 of the sixty-four stages is driven in low logic level under the control of the microprocessor 5, data from the data bus 12, which is eight bits long, is latched in the corresponding latch 13 until a new enable signal takes place. These eight bits determine the frequency and the amplitude of the pulses of the specific stage. The first four bits are fed through a connection 14 to a programmable frequency divider 10. These four bits determine how much the pulse rate (frequency) is to be reduced. Next, a fixed divider 9 reduces the pulse rate further by a fixed frequency division. Up to this point, the amplitude of the pulses remains unchanged. The programmable gain amplifier 8 defines the final amplitude of the pulses. The remaining four bits which are latched from the data bus 12 of the microprocessor are used for this purpose. In the same manner, the frequency and the amplitude of all of the sixty-four stages is defined. The number of stages can be less than, equal to, or more than sixty-four.

Table A below gives the recorded characteristics of each of thirty-two points which correspond to epileptic foci and which were stored in one integrated circuit of a microprocessor which energized the electronic device for the magnetic smoothing of epileptic foci. The left and right parts of Table A give the points of the left and right hemisphere of the brain, respectively. The symbols Pt.#, B(PT) and Hz represent the points which were measured on a patient's skull, the amplitudes of the power spectrum in PT, and their frequencies for the smoothing of the epileptic foci, respectively.

TABLE A

| LEFT SIDE | | | | | | RIGHT SIDE | | | | | |
| --- | --- | --- | --- | --- | --- | --- | --- | --- | --- | --- | --- |
| Pt.# | Hz | B(T) | Pt.# | Hz | B(T) | Pt.# | Hz | B(T) | Pt.# | Hz | B(T) |
| 01 | 2 | 6 | 21 | 2 | 6 | 01 | 4 | 6 | 21 | 5 | 6 |
| 02 | 7 | 6 | 22 | 5 | 6 | 02 | 2 | 6 | 22 | 4 | 6 |
| 03 | 3 | 6 | 23 | 5 | 6 | 03 | 5 | 6 | 23 | 4 | 6 |
| 04 | 2 | 6 | 24 | 7 | 6 | 04 | 2 | 6 | 24 | 4 | 6 |
| 05 | 5 | 6 | 25 | 2 | 6 | 05 | 2 | 6 | 25 | 4 | 6 |
| 06 | 5 | 12 | 26 | 7 | 6 | 06 | 2 | 6 | 26 | 7 | 6 |
| 07 | 2 | 12 | 27 | 7 | 12 | 07 | 5 | 6 | 27 | 3 | 12 |
| 08 | 2 | 12 | 28 | 2 | 6 | 08 | 2 | 6 | 28 | 2 | 6 |
| 11 | 2 | 6 | 31 | 2 | 6 | 11 | 2 | 6 | 31 | 5 | 6 |
| 12 | 7 | 12 | 32 | 6 | 6 | 12 | 2 | 6 | 32 | 4 | 6 |
| 13 | 7 | 12 | 33 | 2 | 6 | 13 | 4 | 12 | 33 | 4 | 6 |
| 14 | 2 | 6 | 34 | 2 | 6 | 14 | 2 | 6 | 34 | 4 | 6 |
| 15 | 7 | 6 | 35 | 7 | 6 | 15 | 2 | 6 | 35 | 4 | 6 |
| 16 | 6 | 12 | 36 | 7 | 6 | 16 | 6 | 6 | 36 | 2 | 6 |
| 17 | 2 | 12 | 37 | 2 | 6 | 17 | 2 | 6 | 37 | 2 | 6 |
| 18 | 7 | 6 | 38 | 2 | 6 | 18 | 5 | 6 | 38 | 2 | 6 |

We claim:

1. An electronic apparatus for the treatment of an epileptic individual, having an epileptic focal point skull distribution, intensity and frequency as determined by use of a superconducting quantum interference device (SQUID), to inhibit seizure activity, the apparatus comprising:

generating means for generating an alternating low voltage and substantially the same frequency as a magnetic field determined to be emitted from each said epileptic focal point;

emitting means electrically connected to said generating means for emitting a magnetic field to the skull of the epileptic individual at the skull coordinates of each epileptic focal point, said emitting means comprising a plurality of coils; and microprocessor means electrically connected to said emitting means for selecting a number of said plurality of coils to which to apply the generated voltage and for regulating the intensity, frequency and waveform of a current applied to the selected coils such that each selected coil emits a magnetic field of substantially the same intensity and frequency as a magnetic field emitted by an epileptic focal point.

2. The apparatus of claim 1, wherein said plurality of coils comprises a group of coils having a plurality of rows of coils, and each of the rows of coils includes a plurality of coils.

3. The apparatus of claim 2, wherein said plurality of coils comprises a plurality of groups of coils.

4. The apparatus of claim 3, wherein each of said groups of coils is mounted to a respective flexible plate in a uniformly spaced arrangement.

5. The apparatus of claim 1, wherein each of said plurality of coils is adapted to emit a magnetic field of a frequency of from about 2 Hz to 7 Hz.

6. The apparatus of claim 1, wherein said microprocessor means comprises a first microprocessor means electrically connected to said emitting means for selecting said selected coils and for regulating the intensity, frequency and waveform of a current applied to said selected coils.

7. The apparatus of claim 6, wherein said first microprocessor means comprises a programmable frequency divider which regulates the frequency of the current applied to said selected coils, and a programmable gain amplifier which regulates the amplitude of the applied current.

8. The apparatus of claim 7, wherein said microprocessor means further comprises a second microprocessor means for controlling the operation of said first microprocessor means.

9. The apparatus of claim 1, wherein said generating means comprises one generator adapted to produce an alternating voltage and a frequency of from about 2 Hz to about 7 Hz.

10. The apparatus of claim 1, wherein said generating means comprises a plurality of generators, and each generator is adapted to produce an alternating voltage and a frequency of from about 2 Hz to about 7 Hz.

11. The apparatus of claim 1, further comprising means for storing the epileptic focal point skull distribution, intensity and frequency information as determined by the SQUID, and for inputting the stored information into said microprocessor means.

12. An electronic apparatus for treating an epileptic individual, having an epileptic focal point skull coordinate distribution, intensity and frequency as determined by a superconducting quantum interference device (SQUID), to inhibit seizure activity, the apparatus comprising:

generator means for generating an alternating voltage and a frequency of from about 2 Hz to about 7 Hz;

a plurality of coil means for emitting a magnetic field to the skull of the epileptic individual at the location of the epileptic focal points;

microprocessor means electrically connected to said emitting means for selecting a number of said plurality of coils to which to apply the generated voltage and for regulating the intensity, frequency and waveform of a current applied to the selected coils such that each selected coil emits a magnetic field of substantially the same intensity as a magnetic field emitted by an epileptic focal point and of a frequency of from about 2 Hz to about 7 Hz; and means for storing the epileptic focal point skull distribution, intensity and frequency information, and for inputting the stored information into said microprocessor means.

13. An electronic apparatus for treating an epileptic individual, having an epileptic focal point skull coordinate distribution, intensity and frequency as determined by a superconducting quantum interference device (SQUID), to inhibit seizure activity, the apparatus comprising:

a plurality of generator means, each of which is adapted to generate an alternating voltage and a frequency of from about 2 Hz to about 7 Hz;

a plurality of groups of coil means for emitting a magnetic field to the skull of the epileptic individual, each of said groups of coil means including a plurality of coils and each of said plurality of coils being adapted to emit a magnetic field of from about 2 Hz to about 7 Hz;

a first microprocessor means electrically connected to said emitting means for selecting a number of said plurality of coils to which to apply the generated voltage and for regulating the intensity, frequency and waveform of a current applied to the selected coils such that each selected coil emits a magnetic field of substantially the same intensity and frequency as magnetic field emitted by an epileptic focal point;

means for storing the epileptic focal point skull distribution, intensity and frequency information, and for inputting the stored information into said first microprocessor means; and a second microprocessor means for controlling the operation of said first microprocessor means.

14. The apparatus of claim 13, wherein said first microprocessor means comprises a programmable frequency divider adapted to regulate the frequency of the current applied to the selected coils, and a programmable gain amplifier adapted to regulate the amplitude of the applied current.

15. The apparatus of claim 13, wherein each of said groups of coils is mounted to a respective flexible plate in a uniformly spaced arrangement.

* * * * *